United States Patent [19]

Huettenrauch et al.

[11] Patent Number: 4,965,456
[45] Date of Patent: Oct. 23, 1990

[54] RADIATION GUARD MEANS

[75] Inventors: Gerd Huettenrauch, Uttenreuth; Herbert Schelschshorn, Erlangen, both of Fed. Rep. of Germany

[73] Assignee: Siemens Aktiengesellschaft, Berlin and Munich, Fed. Rep. of Germany

[21] Appl. No.: 355,272

[22] Filed: May 22, 1989

[30] Foreign Application Priority Data

Jun. 8, 1988 [DE] Fed. Rep. of Germany ....... 8807462

[51] Int. Cl.$^5$ ............................................. G21F 3/00
[52] U.S. Cl. ............................. 250/515.1; 250/517.1; 250/519.1
[58] Field of Search ................ 250/515.1, 512.1, 519.1

[56] References Cited

U.S. PATENT DOCUMENTS

| 3,308,297 | 3/1967 | Mansker | 250/515.1 |
| 3,967,129 | 6/1976 | Winkler | 250/517.1 |
| 4,062,518 | 12/1977 | Stivender et al. | 250/519.1 |
| 4,255,667 | 3/1981 | Bolin et al. | 250/515.1 |
| 4,280,056 | 7/1981 | Renshaw | 250/515.1 |
| 4,460,833 | 7/1984 | Malamud et al. | 250/515.1 |
| 4,581,538 | 4/1986 | Lenhart | 250/515.1 |

Primary Examiner—Jack I. Berman
Assistant Examiner—Kiet T. Nguyen

[57] ABSTRACT

A radiation shielding device having a radiation shielding wall that absorbs x-rays, the wall being mounted on a displaceable carriage on a height adjustable mounting member, the shielding wall including two wall members, the first wall member being arranged under the second wall member, the second wall member being made of a transparent material and being pivotal about a horizontal axis.

24 Claims, 2 Drawing Sheets

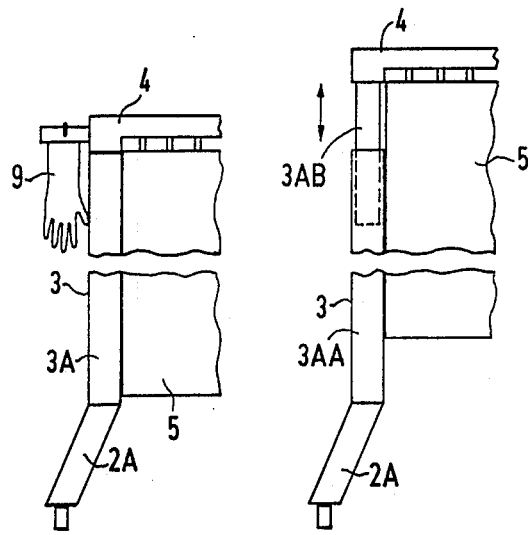
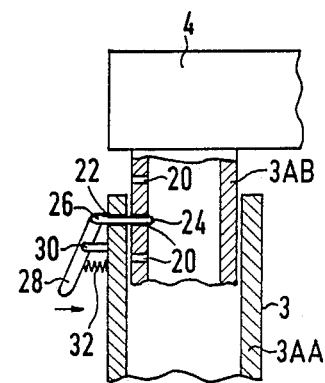
FIG 2  FIG 3  FIG 4
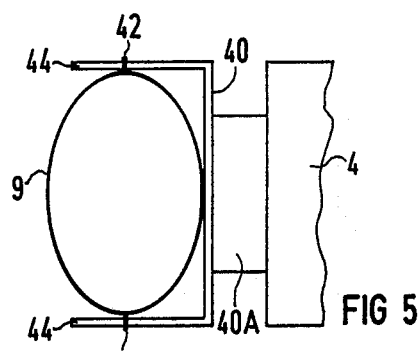
FIG 5
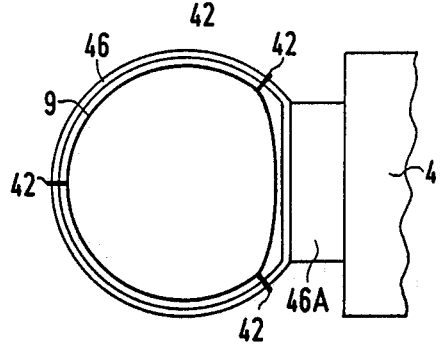
FIG 7
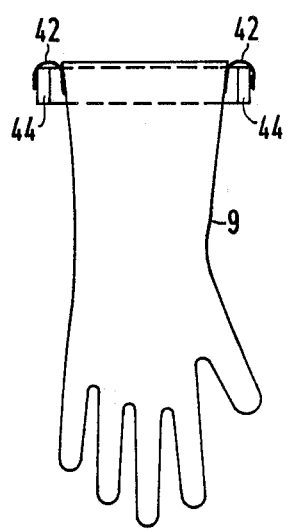
FIG 6

RADIATION GUARD MEANS

BACKGROUND OF THE INVENTION

The present invention generally relates to radiation shielding devices for protecting a person from exposure to radiation. More particularly, the invention relates to a radiation shielding device employed by a person conducting an x-ray examination.

In the radiological examination of a patient, precautions must be taken by the person conducting the examination, such as a radiologist to avoid undue exposure to an impermissibly high dosage of radiation. This is particularly true when patient-proximate examinations are involved that are carried out employing x-ray apparatus comprising above-the-table radiators.

For protection against radiation, a radiologist generally wears a lead-rubber cloak during patient-proximate examinations. Due to its high weight, however, a lead-rubber cloak places a great physical strain on the radiologist, particularly during longer examinations or operations, and is cumbersome due to its lack of flexibility. Moreover, the head and, in particular, the eyes of the radiologist are not protected from radiation by the cloak.

A further radiation shielding measure can be provided by securing lead-rubber curtains to the ceiling of the room or to the examination apparatus. Such lead-rubber curtains, however, can impede the radiologist during his work. Moreover, the curtains can touch and bother the patient.

SUMMARY OF THE INVENTION

The present invention provides a radiation shielding device that offers whole-body radiation protection while not impeding or burdening a person conducting an examination. To this end, the invention provides a radiation guard device that is displaceable along a floor and that includes adjustable shielding wall members. One wall member is mounted above the other to protect the face and head of the person conducting the examination. The other wall member shields the upper and lower body of the person from the radiation.

In an embodiment, the invention provides a carriage member that carries a shield member, the carriage member being freely displaceable. The carriage further includes a mounting member for two wall members comprising the shield member, the mounting member being mounted on the carriage in height adjustable fashion. One wall member is positioned beneath another transparent wall member. The transparent wall member is pivotable about an axis so as to be adjustable.

An advantage of the invention is that the head and, particularly, the eyes of a person conducting an examination are protected against exposure to radiation while still being afforded a clear view of the work area and a patient through the transparent wall member.

Another advantage of the invention is that the person conducting the examination is freed from wearing heavy and cumbersome lead-rubber aprons, this alleviating physical stress on the examiner, especially during longer examinations or operations.

Yet a further advantage of the invention is that additional radiation protection can be provided by increasing the thickness of the various wall members without placing greater weight on the examiner.

These and other advantages will become apparent from the following description of the preferred embodiment thereof, taken in conjunction with the accompanying drawings.

BRIEF DESCRIPTION OF THE DRAWINGS

FIG. 2 is a fragmentary front view of the embodiment of FIG. 1 illustrating the device in its lower position;

FIG. 3 is a fragmentary front view of the embodiment of FIG. 1 illustrating the device in its raised position;

FIG. 4 is a fragmentary cross-sectional view of a stand member of the embodiment of FIGS. 1-3;

FIG. 5 is a top view illustrating a first arrangement for mounting a glove to the embodiment of FIG. 1;

FIG. 6 is a side view of the first arrangement of FIG. 5 for mounting a glove to the embodiment of FIG. 1; and FIG. 7 is a top view of a second arrangement for mounting a glove to the embodiment of FIG. 1.

DETAILED DESCRIPTION OF THE PRESENTLY PREFERRED EMBODIMENT

Figure 1:
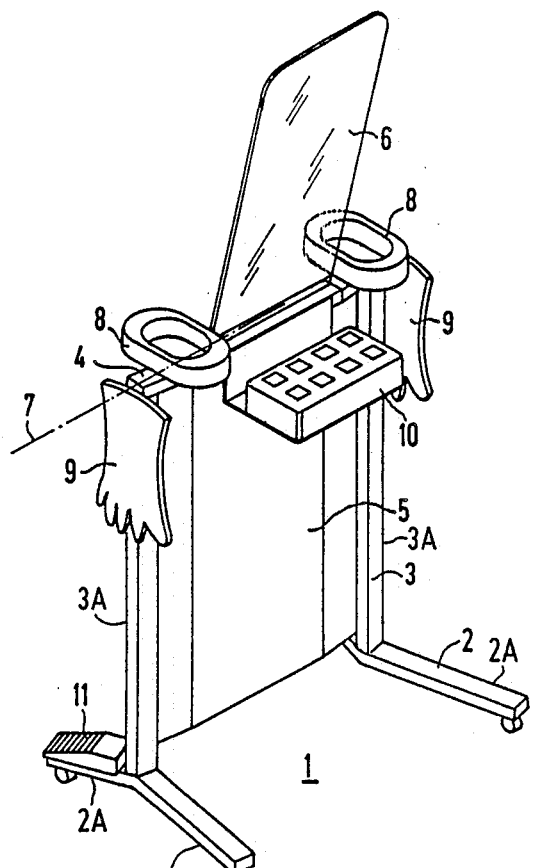
FIG. 1 is a perspective view of an embodiment of the invention.

The presently preferred embodiment of the invention is illustrated in FIG. 1. Therein, there is illustrated a radiation shielding device or radiation guard 1.

The radiation shielding device 1 includes a carriage member 2 to which is mounted a mounting member 4 via a stand 3. The mounting member 4 generally comprises a beam secured to ends of vertical supports 3A forming the stand 3, and is aligned essentially parallel to the floor (i.e., horizontally) and holds and supports two wall members 5 and 6. The wall members 5 and 6 serve to absorb radiation such as x-ray radiation.

As illustrated, the carriage 2 includes four legs 2A that project substantially a right angle to the vertical beams 3A. Accordingly, the legs 2A are disposed substantially horizontally slightly above the floor. Each leg 2A is supported at an end thereof, on a wheel member 2B, such as a caster wheel.

The wall member 5 is positioned relatively beneath or below the wall member 6 and is composed of a suitable x-ray absorbing material such as lead-rubber. The wall member 5 extends from the mounting member 4 down to about floor level.

It can be appreciated that the wall member 5 can comprise a stiff panel or a flexible member such as a curtain.

The other wall member 6 is pivotally secured to the mounting member 4, but on a topside thereof. The wall member 6 is composed of a suitable transparent x-ray shielding material, preferably lead glass. The wall member 6 pivots along a horizontal axis that is parallel to the mounting member 4.

The height of the radiation shield 1 is such that the height of the mounting member 4 falls within the upper body region of an average person. Accordingly, the height of the top of the wall member 6 is chosen so as to extend above the height of the average person, such that the wall member 6 projects above the head of such person. Thus, the head and, in particular, the eyes of the person conducting an examination are shielded from radiation while the person stands behind the radiation guard 1.

The wall member 6 is dimensioned to have a width such that the width of at least the upper body of a person is protected. Accordingly, the freedom of movement of the arms of the person conducting the examination is not restricted in the direction of a work area side of the radiation guard 1. Thus, the width of the wall member 6 is selected so that the person conducting an examination, such as a radiologist, can comfortably reach around the wall member 6 and freely access the work area.

It can be appreciated that recesses (not illustrated) can be provided at appropriate locations along the edges of the wall member 6. Such recesses are adapted to accept the arms of a person. Thus, yet greater freedom of movement and access to the work area can be provided, albeit at a cost of reduced shielding.

It can also be appreciated that the wall member 6 can be mounted as a window that extends above the height of the person conducting an examination. To this end, the wall member 6 is transparent so as to permit viewing therethrough.

In order to adapt the radiation guard 1 to the individual requirements of the person conducting the examination, the mounting member 4 is adjustable in height by means of the stand 3. That is to say, the individual vertical members 3A and 3B of the stand 3 can be made so as to be height adjustable. Moreover, the wall member 6 is pivotable about the longitudinal axis 7 of the horizontal mounting member 4. As a result, the radiation guard 1 can be set to the particular needs of a person and in view of the particular conditions of the work area, to thereby afford optimal radiation shielding.

The presently contemplated manner in which the stand 3 and mounting member 4 are height adjustable, is illustrated more particularly in FIGS. 2-4. As illustrated, each vertical support 3A of the stand 3 includes a lower leg portion 3AA and an upper leg portion 3AB. The upper leg portion 3AB is accommodated and received within the lower leg portion 3AA. Accordingly, the leg portions 3AA and 3AB cooperate in telescoping fashion so that the mounting member 4, which is attached to the upper leg portion 3AB, is permitted to be raised and lowered relative to the lower leg portion 3AA.

It can be appreciated that as the mounting member 4 is lowered and raised, the wall member 5 attached thereto also is lowered and raised. Accordingly, the gap formed between the bottom of the wall member 5 and the floor increases as the mounting member 4 is raised and decreases as the mounting member 4 is lowered.

In FIG. 4, a contemplated mechanism for fixing or locking the position of the upper leg portion 3AB relative to the lower leg portion 3AA is illustrated. In the illustrated mechanism, openings such as bores are formed in sides of both leg portions 3AA and 3AB. A plurality of bores 20 are formed in the upper leg portion 3AB while only a single opening 22 is formed in the lower leg portion 3AA. It can be appreciated that, as the upper leg portion 3AB is moved up or down relative to the lower leg portion 3AA, the opening 22 will occasionally register with one of the openings 20. When the mounting member 4 is at the selected height and the opening 22 is in registry with an opening 20, a pin 24 is inserted through all of the openings so as to lock the leg portions 3AA and 3AB in position relative to each other.

The pin 24, as illustrated, is pivotally attached at 26 to a lever arm 28 which in turn is pivotally attached at 30 to the lower leg portion 3AA and be biased by means of a spring 28 32 in an engaging direction (i.e., biased toward the interior of the lower leg portion 3AA). Accordingly, one needs only to lever the pin 24 in and out of the openings 20 by means of the spring biased articulation, while adjusting the height of the mounting member 4.

During therapeutic irradiation, it can be especially advantageous to provide support to the person conducting the examination. To this end, support shells or members 8 are provided along the mounting member 4 on opposite sides of the wall member 6. It can be appreciated that the support members 8 are adapted to comfortably receive therein the elbows or arms of the examining person. The legs and upper body of the examining person can thereby be relieved. As a result, working in the examining area is facilitated.

As illustrated, the support members 8 are positioned on opposite sides of the wall member 6 on the mounting member 4, and, accordingly, are also adjustable in height. Thus, the height of the support members 8 can be adjusted according to the individual needs of various persons by adjusting the height of the mounting member 4. However, it can be appreciated that the support members 8 can be mounted on additional supports so that the support members 8 are separately adjustable in height.

An advantage of providing the support shells 8 on the radiation guard 1 is that the person conducting the examination can easily cause the radiation guard 1 to be laterally displaced along the floor by pushing the radiation guard 1 with his/her elbows or forearms while such person's arms are engaged in the support members 8. The hands of such person can remain sterile inasmuch as they need not contact anything. Thus, the provision of the support members 8 is an especially helpful advantage in an operating area or situation, or in any area or situation where the examining person's hands must be sterile.

If the examining person is required to act in an operating (or otherwise sterile) area during an examination (or trans-illumination), then lead gloves are needed. To this end, lead gloves 9 are provided and retained on mounts, not illustrated, on opposite lateral sides of the mounting member 4. The glove mounts are designed to allow single-handed placement of a glove 9 on a hand.

The presently contemplated structures for locating and mounting the gloves 9 to the mounting member 4 is illustrated more particularly in FIGS. 5-7. Two similar structures are contemplated.

In FIGS. 5 and 6, a U-shaped clip member 40 is illustrated as being attached to a longitudinal end of the mounting member 4 by means of a spacer member 40A. The clip member 40 is attached so that the U-shape profile is seen from above and below along the vertical dimension of the radiation guard 1.

A glove 9 includes hook members 42 attached thereto, the hook members 42 operatively engaging top edges of horizontally exerting arms 44 of the clip member 40. Accordingly, whenever a glove 9 is attached to the radiation guard 1, the glove 9 hangs from a clip member 40 by means of the hook member 42.

It can be appreciated that the distance between the arms 44 of the clip member 40 is selected so that when the hook members 42 engage the top edges thereof, a glove 9 is held in a slightly open state. Accordingly, one can slip the glove 9 on simply by inserting a hand into the glove 9. There is no need to employ the assistance of the other hand. Therefore, the described structure allows for one-hand or single-handed placement of a glove 9 on a hand.

After the glove 9 has been slipped on, the person wearing the glove can remove his or her hand with glove engaged thereon by moving the hand either laterally or in an upward direction.

It can be further appreciated that the described structure is especially beneficial for stiffer gloves inasmuch as such gloves will more readily be held open when hung from a clip member 30.

If the glove 9 is made of a softer, more flexible material and, accordingly, is not likely to be held in an open position on the clip member 4, then the structure illustrated in FIG. 7 can be employed. As illustrated, the clip member 4 is replaced with a hoop member 46, which hoop member 46 includes an upper edge that surrounds the glove 9. The hoop member 46 is similarly attached to the mounting member 4 by means of a spacer member 46A. Further, at least one additional hook member 42 is attached to the glove 9.

As illustrated, the employment of the hoop member 46 allows the hook member 42 to engage the top edge at various locations spaced apart about a circumference so as to force the glove 9 to be held in an open position. The glove 9 is slipped on simply by inserting one's hand into the glove 9. After the glove 9 is slipped on, the person wearing the glove removes his or her hand (with glove engaged thereon) in an upward direction.

A unit 10 for controlling the main functions of a radiation diagnostic system or installation (preferably an x-ray diagnostics installation) and a patient bed (not illustrated) is provided and secured to the face of the mounting unit 4 facing toward the examination region. It can be appreciated that the unit 10 can be mounted so as to swivel about the axis 7 of the mounting member 4 so that the unit 10 can be swung out of the examination region when not required. The unit 10 can be, and is, designed to be, employed by the person conducting an examination to comfortably operate operating elements of the x-ray diagnostics system.

In an especially advantageous embodiment, the unit 10 cooperates with the x-ray diagnostics system in a non-physically coupled manner, i.e., in cable-free fashion. This can be accomplished through a variety of methods including radio transmission coupling. As a result, any danger of tripping over cables and the like attached to the radiation guard 1 is reduced or eliminated. Further, any impediment to displacement of the radiation guard 1 due to a cable lying on the floor is also reduced or eliminated.

As further illustrated, the radiation guard 1 can be, and is, advantageously provided with a foot-operated switch (foot switch) 11. The foot switch 11 can be employed to trigger x-ray exposure. The foot switch 11 is mounted on one of the legs 2A of the carriage member 2.

As illustrated, the foot switch 11 also operates in cable free fashion. As a result, the radiation guard 1 can be displaced freely along a floor without being impeded by cables attached thereto.

It can be appreciated from the foregoing that the radiation guard 1 provides whole body radiation shielding. However, a person conducting an examination need not wear a cumbersome and heavy lead-rubber cloak.

While a preferred embodiment has been shown, modifications and changes may become apparent to those skilled in the art which shall fall within the spirit and scope of the invention. It is intended that such modifications and changes be covered by the attached claims.

We claim as our invention:

1. Radiation shielding means comprising:
    (a) a freely displacing carriage constructed to carry a radiation shielding wall;
    (b) a mounting member carried on said carriage, said mounting member being height adjusted; and
    (c) a radiation shielding wall supported by said mounting member including two wall members, said first wall member being positioned below said second wall member, said second wall member comprising a transparent element, and said second wall member being pivoted around a horizontal axis, said radiation shielding wall shielding upper and lower portions of a body against radiation.

2. The radiation shielding means of claim 1, wherein said mounting member is a beam arranged on a horizontal axis approximately parallel to the floor.

3. The radiation shielding means of claim 1, wherein the first wall member is made of lead-rubber and is mounted such that an end thereof is positioned above a level of the floor, and wherein the second wall member is made of lead-glass and has an upper end that extends above a height of a person.

4. The radiation shielding means of claim 1, wherein the supporting members for supporting arm portions of a person are provided adjacent the mounting member.

5. The radiation shielding means of claim 1, further including a unit attached to the mounting member, said unit comprising controls for controlling an x-ray diagnostics system.

6. The radiation shielding means of claim 1, further including means for securing lead gloves to the mounting member.

7. The radiation shielding means of claim 1, wherein the carriage includes a foot switch attached thereto.

8. A device for shielding a person conducting an x-ray examination from radiation, comprising:
    (a) a carriage member that is displaced along a floor, said carriage member including two vertical supporting members having top and bottom ends and leg members extending from bottom ends of said supporting members;
    (b) a mounting member secured on said carriage member on said vertical supporting members;
    (c) a first radiation shielding wall member secured to said mounting member and extending from said mounting member to a bottom end of said carriage member; and
    (d) a second radiation shielding wall member pivotally mounted on said mounting member above said wall member.

9. The device of claim 8, wherein the carriage member includes wheels attached to a bottom side thereof.

10. The device of claim 8, wherein the second radiation shielding wall member is transparent.

11. The device of claim 10, wherein the second radiation shielding wall member comprises lead glass.

12. The device of claim 8, wherein the first radiation shielding wall member comprises lead-rubber.

13. The device of claim 8, further comprising a control unit for controlling functional elements of an x-ray installation.

14. A device for shielding a person from x-ray radiation, comprising:
    (a) carriage means for supporting shielding elements, said carriage means including two vertically upstanding supporting members, each supporting member having extending from a bottom thereof legs to which are attached wheels and being laterally displaced along a floor;

(b) mounting means for mounting radiation shielding elements on the carriage means, the mounting means including a horizontal mounting member attached to free ends of the two upstanding vertical supporting members;

(c) first radiation shielding means supported between the vertically extending members; and (d) second radiation shielding means pivotally supported on the mounting member above the first radiation shielding means.

15. The device of claim 14, wherein the second radiation shielding means comprises a transparent wall element.

16. The device of claim 15, wherein the transparent wall element comprises a lead glass panel.

17. The device of claim 14, wherein the first radiation shielding means comprises a lead rubber panel.

18. The device of claim 14, wherein the second radiation means is pivotally supported on the mounting member so as to be pivotable about a horizontal axis.

19. The device of claim 14, wherein:
the first radiation shielding means comprises a lead-rubber panel;
the second radiation shielding means comprises a transparent lead glass panel, the lead glass panel being pivotally mounted on the mounting member so as to pivot about a horizontal axis; and
the vertical members being adjustable in height.

20. A device comprising:

(a) mounting means for supporting a wall member in vertical relationship to the floor;

(b) first wall means for shielding against radiation attached and secured to said mounting means, said first wall means operatively adapted to shield a person's body from radiation, said first wall means being positioned substantially at right angles to the floor;

(c) second wall means for shielding against radiation attached and secured to said mounting means, said second wall means operatively adapted to shield a person's face from radiation, said second wall means being pivotally mounted to said mounting means to pivot about an axis parallel to the floor; and (d) carriage means on which said mounting means is mounted for carrying said mounting means, said first wall means, and said second wall means in lateral fashion across the floor, said carriage means including two vertically upstanding members supporting a horizontal beam, said two vertically upstanding members being positioned on opposite sides of said first wall means, said two vertically upstanding supporting members including legs extending from bottom ends thereof.

21. The device of claim 20, wherein the second wall means is transparent lead-glass.

22. The device of claim 20, wherein the carriage means includes wheels attached to an underside of the carriage means.

23. The device of claim 20, wherein the mounting means is vertically adjustable.

24. The device of claim 20, wherein the first wall means comprises lead-rubber.

* * * * *